United States Patent [19]

Nakao et al.

[11] Patent Number: 5,486,182

[45] Date of Patent: Jan. 23, 1996

[54] POLYP RETRIEVAL ASSEMBLY WITH SEPARABLE WEB MEMBER

[75] Inventors: Naomi L. Nakao; Peter J. Wilk, both of New York, N.Y.

[73] Assignee: Wilk & Nakao Medical Technology Inc., New York, N.Y.

[21] Appl. No.: 213,196

[22] Filed: Mar. 14, 1994

Related U.S. Application Data

[63] Continuation-in-part of Ser. No. 12,657, Feb. 1, 1993, Pat. No. 5,336,227, which is a continuation-in-part of Ser. No. 788,035, Nov. 5, 1991, Pat. No. 5,201,740, and Ser. No. 892,214, Jun. 2, 1992, Pat. No. 5,190,542.

[51] Int. Cl.⁶ .......................... A61B 17/22; A61B 17/36
[52] U.S. Cl. ................. 606/114; 606/110; 600/37
[58] Field of Search ........................ 606/1, 106, 110, 606/113, 114, 127, 128, 151, 37–40, 45–52; 600/37; 128/749–754

[56] References Cited

U.S. PATENT DOCUMENTS

| | | | |
|---|---|---|---|
| 460,940 | 10/1891 | Baugh | 606/106 |
| 1,609,014 | 11/1926 | Dowd | 606/114 |
| 3,472,230 | 10/1969 | Fogarty | 606/127 |
| 3,715,829 | 2/1973 | Hamilton | 43/12 |
| 4,202,338 | 5/1980 | Bitrolf | 606/47 |
| 4,326,530 | 4/1982 | Fleury, Jr. | 606/47 |
| 4,345,599 | 8/1982 | McCarrell | 606/113 |
| 4,493,320 | 1/1985 | Treat | 606/47 |
| 4,503,855 | 3/1985 | Maslanka | 606/47 |
| 4,516,347 | 5/1985 | Dickie | 43/11 |
| 4,557,255 | 12/1985 | Goodman | 606/127 |
| 4,638,802 | 1/1987 | Okada | 606/47 |

(List continued on next page.)

FOREIGN PATENT DOCUMENTS

| | | | |
|---|---|---|---|
| 0025796 | 1/1884 | Brazil | 606/127 |
| 0046856 | 5/1889 | Germany | 606/45 |

OTHER PUBLICATIONS

Waye, J. D. et al. "The Lost Polyp: a Guide to Retrieval during Colonoscopy" *Int. J Colorect Dis* (1988) 3:229–231.

Ricca, J. J. "Retrieval of Polyps Severed at Colonoscopy" *Gastrointestinal Endoscopy* (1977) 24, 1:44.

Maas, L. C. et al. "Polyp Retrieval Impossible Without Colonoscopy Tip" and Ward, W. J. Reply *Gastrointestinal Endoscopy* (1984) 30 6:378.

Abrams, J. S. "A Hard Look at Colonoscopy" *The American Journal of Surgery* (Jan. 1977) 133:111–115.

Schwesinger, W. H. "Complications in Colonoscopy" *Surgery, Gynecology & Obstetrics* (Feb. 1979) 148:270–281.

Sugarbaker, P. H. "Colonoscopy in the Management of Diseases of the Colon and Rectum" *Surgery, Gynecology & Obstetrics* (Sep. 1974) 139:341–349.

Kobayashi, S. "Colonoscopic Polypectomy With Special Reference To Management of Multiple Polyps" (Kitano H. et al.) *Gastro Endosc* (1983) 29, 4:335–6.

*Primary Examiner*—Stephen C. Pellegrino
*Assistant Examiner*—Glenn Dawson
*Attorney, Agent, or Firm*—R. Neil Sudol; Henry D. Coleman

[57] ABSTRACT

A surgical instrument assembly for use in snare cauterization operations includes a tubular sheath member, a cauterization loop, and a wire operatively connected to the loop, the wire passing longitudinally through the sheath. An electrical supply is connected to the wire for feeding an electrical current to the loop, while an actuatable shifter is connected to the wire for sliding the wire along the sheath. A flexible web member is removably attached to the loop to form a capture pocket. During use the loop is passed over a polyp to be removed so that the web member substantially surrounds the polyp. The loop is then closed to engage the polyp around a base region thereof and an electrical current is conducted through the loop to burn through the polyp at the base region. The severed polyp is automatically captured by the web member. The web member is substantially separated from the loop allowing the loop to be retracted into the sheath while allowing the web member and captured polyp to remain outside the sheath.

15 Claims, 13 Drawing Sheets

U.S. PATENT DOCUMENTS

| | | | |
|---|---|---|---|
| 4,643,187 | 2/1987 | Okada | 606/47 |
| 4,718,419 | 1/1988 | Okada | 128/4 |
| 4,997,435 | 3/1991 | Demeter | 606/127 |
| 5,037,379 | 8/1991 | Clayman et al. | |
| 5,084,054 | 1/1992 | Bencini et al. | 606/127 |
| 5,122,147 | 6/1992 | Sewell | 606/113 |
| 5,143,082 | 9/1992 | Kindberg et al. | |
| 5,147,371 | 9/1992 | Washington et al. | |
| 5,158,561 | 10/1992 | Rydell et al. | |
| 5,190,542 | 3/1993 | Nakao et al. | 606/113 |
| 5,201,740 | 4/1993 | Nakao et al. | 606/113 |
| 5,279,539 | 1/1994 | Bohan et al. | 606/110 |
| 5,312,416 | 5/1994 | Spaeth et al. | 606/110 |
| 5,341,815 | 8/1994 | Cofone et al. | 600/37 |
| 5,354,303 | 10/1994 | Spaeth et al. | 606/113 |
| 5,368,597 | 11/1994 | Pagedas | 606/114 |

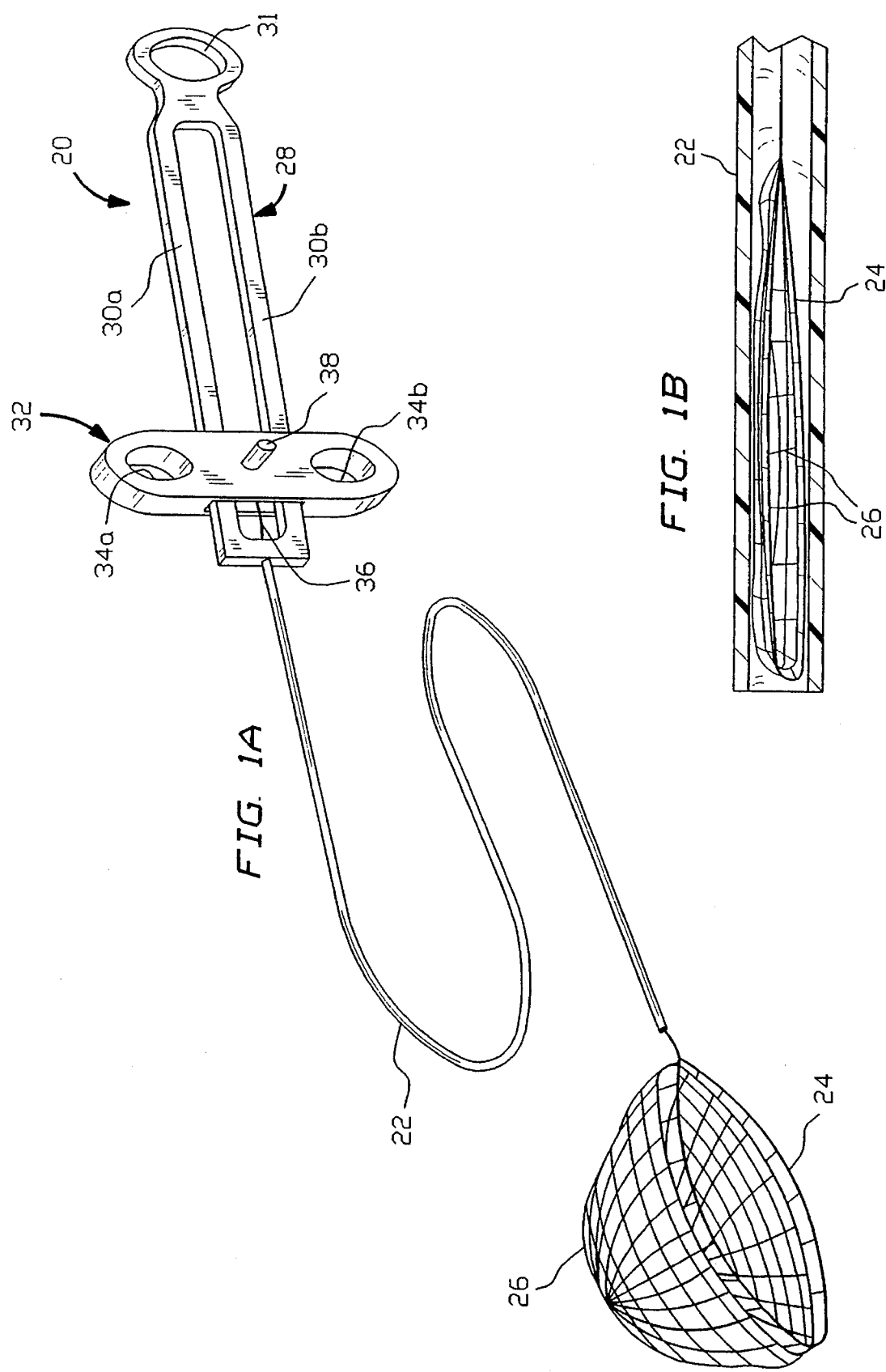

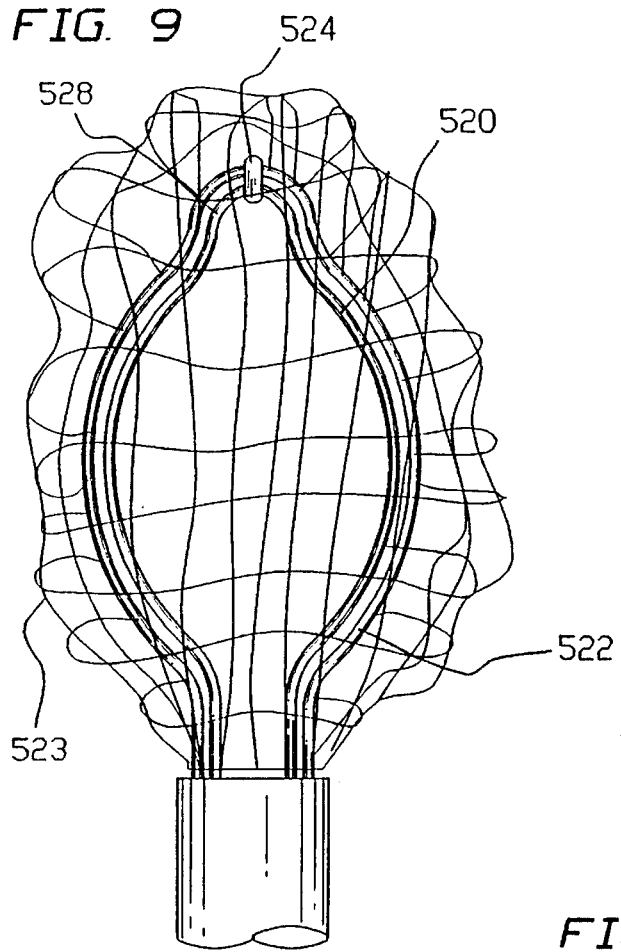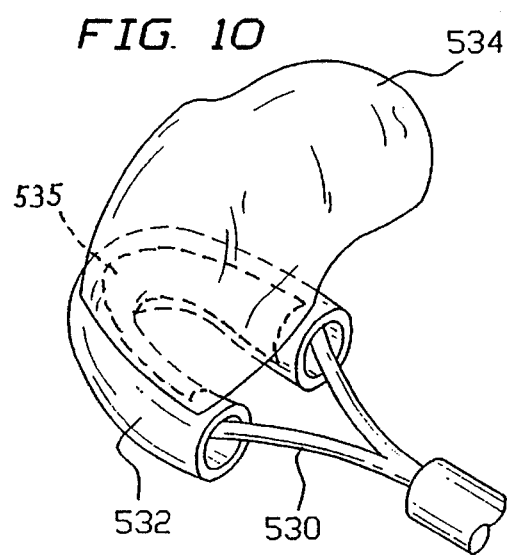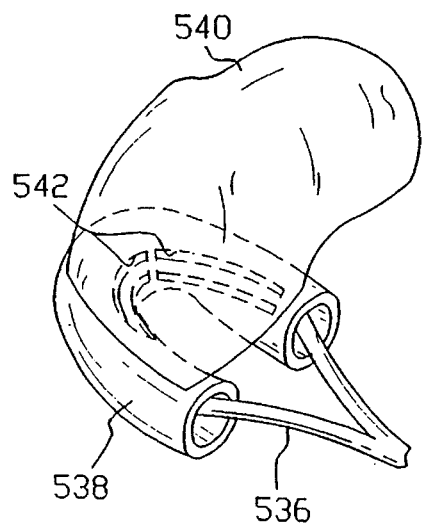

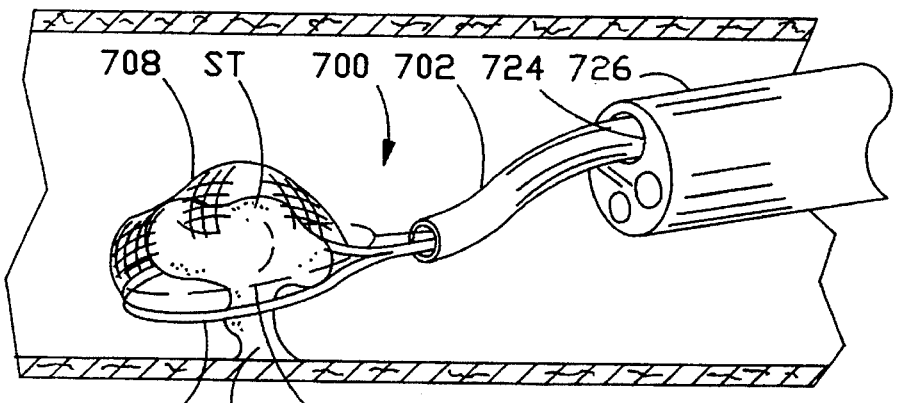
FIG.19A
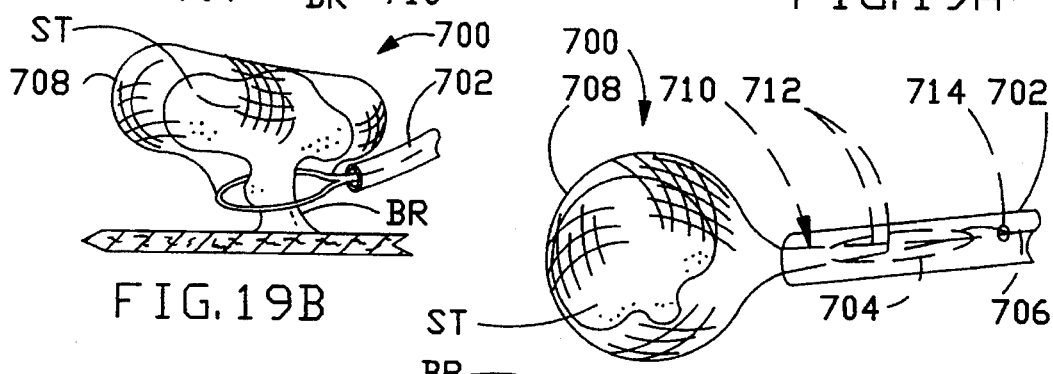
FIG.19B
FIG.19C
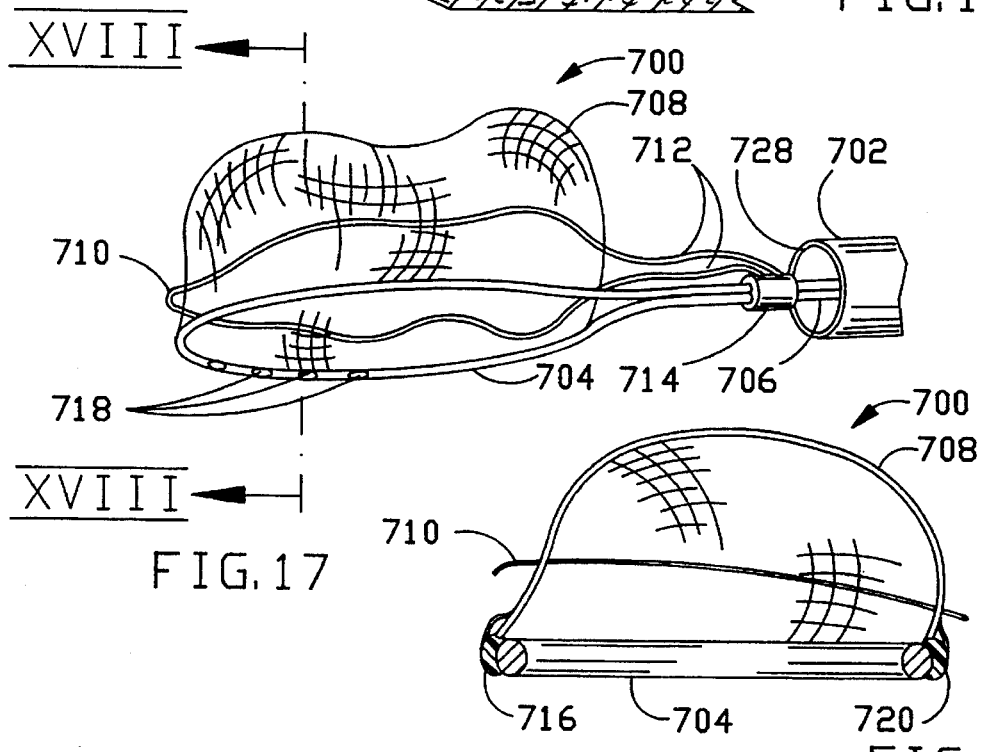
FIG.17
FIG.18

5,486,182

POLYP RETRIEVAL ASSEMBLY WITH SEPARABLE WEB MEMBER

CROSS-REFERENCE TO RELATED APPLICATIONS

This application is a continuation-in-part of commonly owned application Ser. No. 08/012,657 filed Feb. 1, 1993, now U.S. Pat. No. 5,336,227 as a continuation-in-part of commonly owned application Ser. No. 07/788,035 filed Nov. 5, 1991, now U.S. Pat. No. 5,201,740, and a continuation-in-part of commonly owned application Ser. No. 07/892,214 filed Jun. 2, 1992, now U.S. Pat. No. 5,190,542.

FIELD OF THE INVENTION

This invention relates to a surgical instrument assembly for use in retrieving objects from internal body cavities. This invention also relates, more specifically, to a surgical instrument assembly for use in snare cauterization operations. This invention also relates to a related method for retrieving objects from internal body cavities and more particularly to a method for capturing and/or retrieving polyps and other clumps of organic tissue which have been severed from a patient's internal organs via a snare cauterization technique.

BACKGROUND OF THE INVENTION

In a conventional snare operation, an endoscope is inserted into an internal cavity of a patient, e.g., into the colon, and is used to locate abnormal tissue growths such as polyps in the internal cavity. Upon the locating of a polyp or other growth which is Lo be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmittted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

Furthermore, there are numerous cases where a severed polyp is never recovered. Sometimes, the polyp is masticated during the retrieval attempt. In all such cases, the pathologist is unable to determine whether the polyp contains carcinoma in situ (localized) or infiltrative carcinoma (spread). The patient must then undergo a colon resection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

OBJECTS OF THE INVENTION

An object of the present invention is to provide an improved method for the removal of portions of internal body organs or other objects from patients.

A more specific object of the present invention is to provide an improved method for the performance of snare cauterization.

Another object of the present invention is to provide a snare cauterization technique wherein the capture and retrieval of severed polyps is facilitated.

Another, more particular, object of the present invention is to provide a snare cauterization technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

An additional particular object of the present invention is to provide such an instrument assembly which is disposable. Such an instrument assembly requires no lengthy sterilization procedure and reduces the spread of infectitous diseases such as AIDS.

These and other objects will be apparent from the following descriptions.

SUMMARY OF THE INVENTION

An endoscopic surgical instrument for use in snare cauterization operations comprises, in accordance with the present invention, a tubular sheath member, an alternately expandable and contractible cauterization loop, an electrically conductive wire operatively connected to the loop, the wire being slidable longitudinally through the sheath, and a flexible web member connected to the loop essentially around a circumference thereof to form a capture pocket. The loop defines a mouth opening of the pocket and is attached to the loop in a manner so as to expose the loop to enable effective cauterization of organic tissues by the loop. The web member is removably attached to the loop along a major portion thereof to enable at least a substantial separation of the web member from the loop upon a proximally directed stroke of the wire at the termination of a cauterization operation.

According to another feature of the present invention, the surgical instrument further comprises a purse string attached to the web member along a ring shaped locus proximately to the mouth opening. The purse string is preferably attached at a proximal end to the wire. More preferably, the purse string is attached to the wire proximate to the distal end thereof. However, it is also possible for the purse string to extend in a proximal direction entirely through the sheath member to the proximal end thereof.

The web member may be attached by adhesive to the loop, either at a plurality of discrete points or along a continuous length of the loop. In addition, it is contemplated that where the loop has a radially outwardly facing surface area, the web member is removably attached to the loop along that radially outwardly facing surface area.

The web member is preferably in the form of a net, but may alternatively take the form of a continuous film of polymeric material.

Accordingly to another feature of the present invention, the web member is permanently attached to the loop only at the distal tip thereof. This permanent attachment serves in part to facilitate an assembly procedure wherein the snare with the substantially (but not completely) separable pocket is inserted into the sheath from the proximal end thereof.

A method for removing a selected portion of internal body tissues of a patient utilizes, in accordance with the present invention, a conductive cauterization loop to which a flexible web member is removably connected to define an expandable pocket. The loop defines a mouth opening of the pocket, while the web member is attached to the loop in a manner so as to expose the loop to enable effective cauterization of organic tissues by the loop. The method comprises the step of (a) ejecting the loop from a distal end of a tubular sheath member, (b) upon ejection of the loop, expanding the loop and the web member from a collapsed configuration to an at least partially opened configuration, and (c) pain, sing the expanded loop over the selected internal body tissues to be removed, so that the web member substantially surrounds the selected internal body tissues. In a subsequent step (d), the loop is drawn back into the distal end of the tubular sheath member, thereby closing the loop around a base region of the selected internal body tissues, while the web member is maintained surrounding the selected internal body tissues. During the drawing of the loop back into the sheath member, (i) an electrical current is conducted through the loop to sever the selected internal body tissues at the base region, (ii) the web member is detached from the loop so that the web member remains outside the sheath member, and (iii) the mouth opening of the web member is closed to thereby capture the severed internal body tissues in the wed member.

According to another feature of the present invention, the web member is detached by being peeled away from the loop at a distal edge of the sheath member. The drawing of the loop back into the distal end of the sheath member draws the capture pocket into contact with a distal edge of the sheath member. That contact forces the capture pocket or web member from the loop.

According to the present invention, the loop is pulled completely into the sheath member upon the termination of a cauterization operation. The web member and the captured internal body tissues remain outside of the sheath member.

The cauterization snare assembly in accordance with the present invention and the associated method of removing a piece of organic tissues (such as a polyp) facilitates use of a cauterization snare assembly as described and claimed in U.S. Pat. No. 5,201,740 and U.S. Pat. No. 5,190,542. A cut by a snare in accordance with the present invention is cleaner and more effective than in those cases where a capture pocket is permanently attached to the cauterization loop and must be partially pulled into the distal end of a sheath to complete a cauterization and capture operation, as described in U.S. Pat. Nos. 5,201,740 and 5,190,542.

The present invention provides an improved method for the removal of portions of internal body organs from patients via snare cauterization.

In a method in accordance with the present invention, the capture and retrieval of severed polyps is facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

A method for assembling a cauterization snare assembly comprises, in accordance with the present invention, the steps of providing a cauterization loop having a capture pocket attached thereto so as to be at least substantially removable from the loop, providing a sheath having a flared distal end, inserting the loop with the capture pocket into the sheath through the flared distal end, and upon disposition of the loop with the capture pocket in a narrowed section of the sheath, severing the flared distal end from the narrowed section.

In another method for assembling a cauterization snare assembly in accordance with the present invention, a film is wrapped around the loop and the capture pocket. Subsequently, the loop and the capture pocket, with the film wrapped therearound, are inserted into a distal end of a sheath. In addition, the film may be bonded to an inner surface of the sheath.

BRIEF DESCRIPTION OF THE DRAWING

FIG. 1A is a schematic perspective view of a snare cauterization instrument assembly, showing a cauterization loop in an ejected, use configuration.

FIG. 1B is a schematic longitudinal cross-sectional view of a distal end of the cauterization instrument assembly of FIG. 1A, showing the cauterization loop in a withdrawn or retracted storage configuration inside the distal end of a tubular member of the instrument assembly.

FIG. 9 is a schematic top view of another modified snare cauterization instrument assembly, showing an auxiliary loop attached at one point to a cauterization loop.

FIG. 10 is a schematic partial perspective view, on an enlarged scale, of an additional snare cauterization instrument assembly.

FIG. 11 is a schematic partial perspective view, on an enlarged scale, of yet a further snare cauterization instrument assembly.

FIG. 17 is a schematic side elevational view, on an enlarged scale, of a cauterization snare assembly in accordance with the present invention.

FIG. 18 is a schematic cross-sectional view, on an enlarged scale, taken along line XVIII—XVIII in FIG. 17.

FIGS. 19A–19C are schematic side elevational views of the cauterization snare assembly of FIGS. 17 and 18, showing successive steps in the use of the assembly of FIGS. 17 and 18, in accordance with the present invention.

DETAILED DESCRIPTION

Figure 2A:
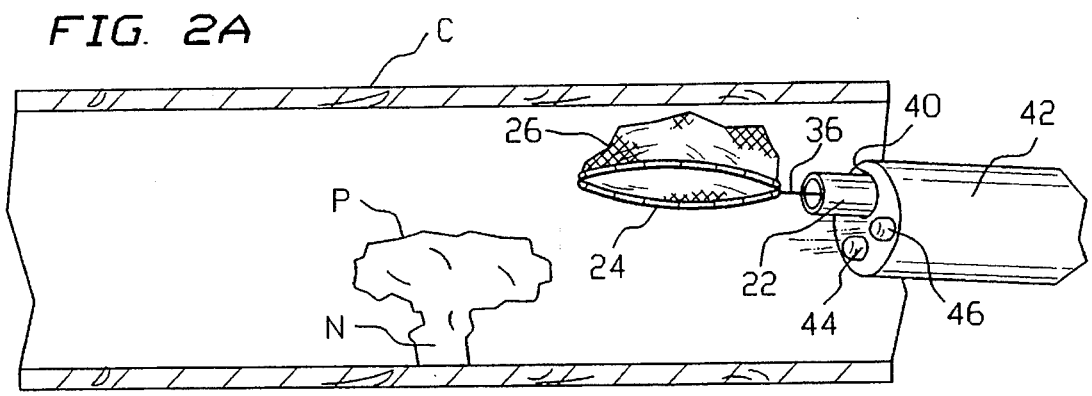
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated in FIG. 1A, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of a wire 36 which passes through tubular member 22 and is in turn connected to cauterization loop 24 at the distal end of tubular member 22. Wire 36 is sufficiently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible transparent synthetic resin or polymeric material such as polyethylene or nylon. Prior to the beginning of a snare cauterization operation, web 26 is disposed in a closed, folded or contracted state, together with loop 24, in the distal end of tubular member 22, as illustrated in FIG. 1B. Concomitantly, slider member 32 is retracted to the proximal end of rails 30a and 30b (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
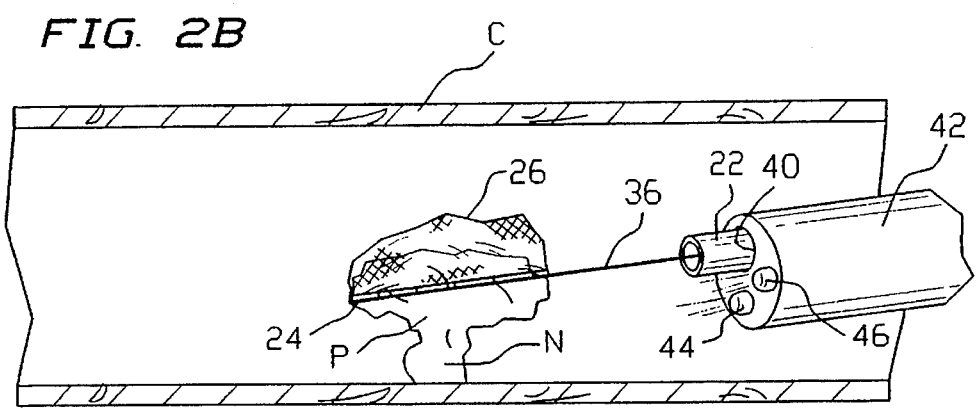
FIG. 2B is a schematic partial cross sectional view similar to FIG. 2A, showing a loop of the snare cauterization instrument assembly of FIG. 1A being passed around the polyp of FIG. 2A.
Figure 2C:
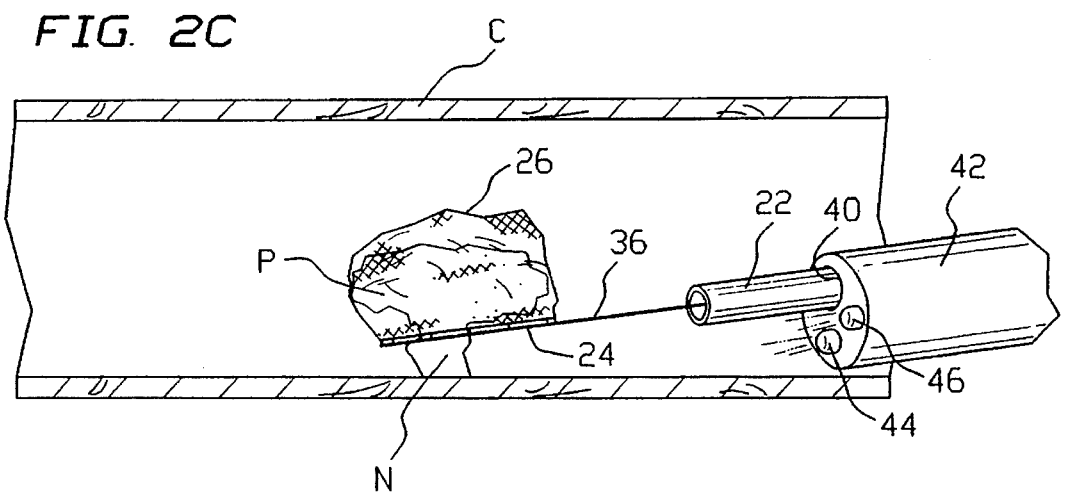
FIG. 2C is a schematic partial cross sectional view similar to FIGS. 2A–2B; showing the loop of the snare cauterization instrument assembly of FIG. 1A completely passed around the polyp of FIG. 2A.

FIG. 2B depicts; a later stage in the cauterization procedure. The snare cauterization instrument assembly of FIG. 1A is manipulated to pass loop 24 around polyp P, with capture web 26 following. Eventually, loop 24 encircles a base region or neck N of polyp P and the polyp is surrounded by capture web 26, as shown in FIG. 2C.

Figure 2D:
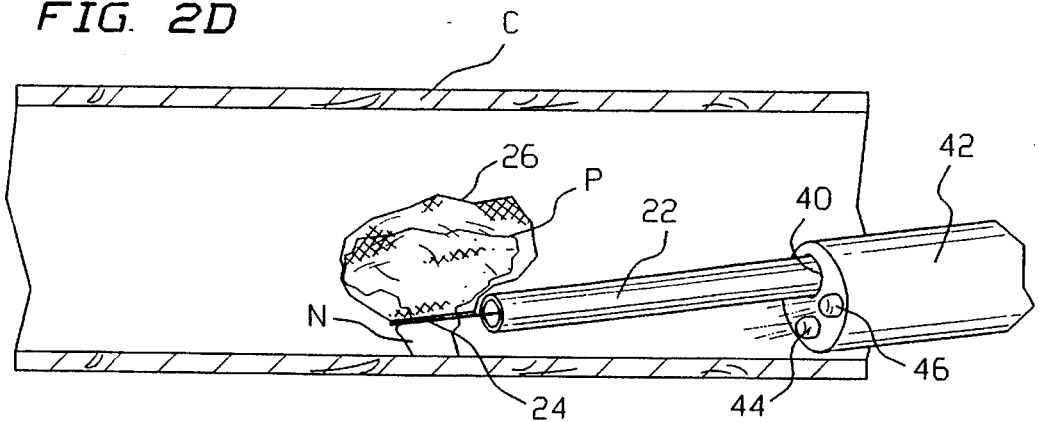
FIG. 2D is a schematic partial cross sectional view similar to FIGS. 2A–2C, showing the loop of the snare cauterization instrument assembly of FIG. 1A being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
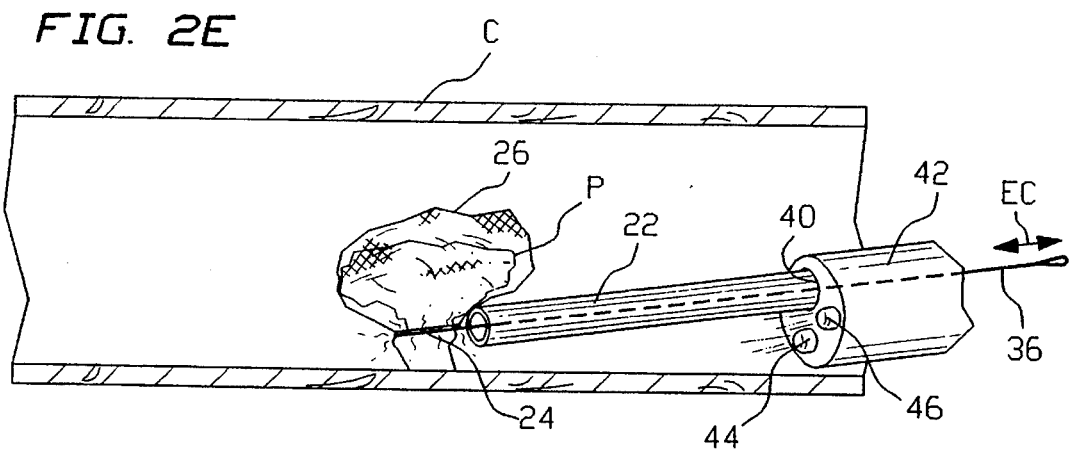
FIG. 2E is a schematic partial cross sectional view similar to FIGS. 2A–2D, showing the loop of the snare cauterization instrument assembly of FIG. 1A in an electrically energized state for burning through the base or neck of the polyp.
Figure 2F:
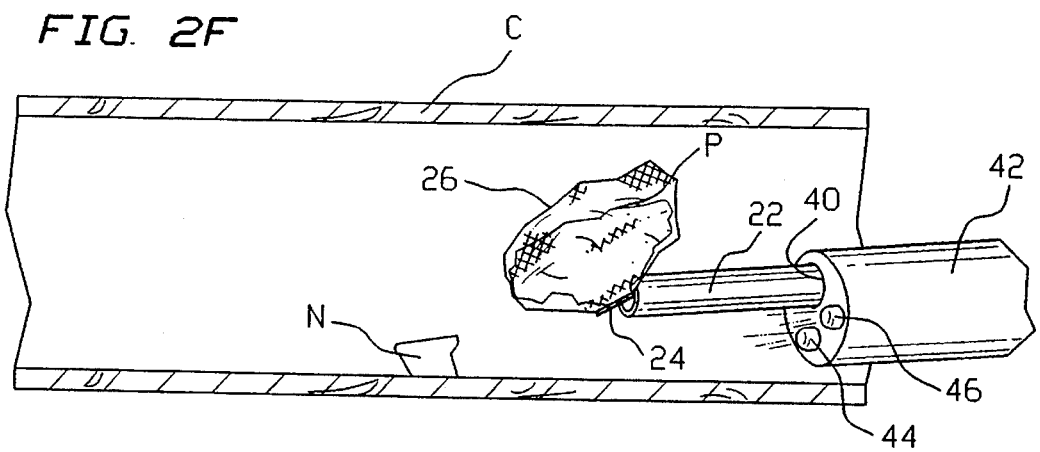
FIG. 2F is a schematic partial cross sectional view similar to FIGS. 2A–2E, showing the polyp severed from the colon wall and captured with the snare cauterization instrument assembly of FIG. 1A.
Figure 2G:
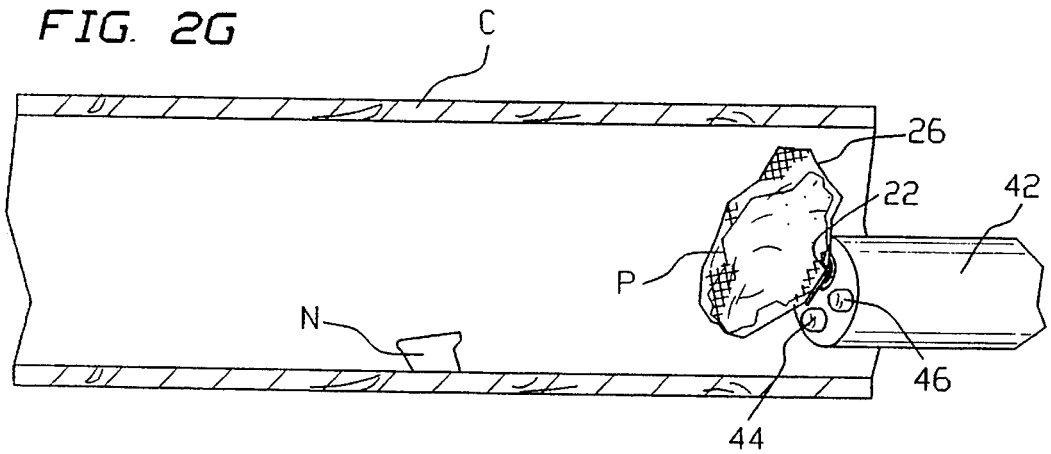
FIG. 2G is a schematic partial cross sectional view similar to FIGS. 2A–2G, showing the snare cauterization instrument assembly of FIG. 1A together with the captured polyp drawn towards the distal end of the endoscope.

As indicated in FIG. 2E, electrical current EC is then caused to pass through wire 36 and loop 24. Generally, electric currect from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22, as shown in FIG. 2F, to essentially close the loop. Polyp P is now securely trapped in capture web 26. In a further step, depicted in FIG. 2G, the entire snare cauterization instrument assembly including, in particular, tubular member 22, is shifted in the proximal direction relative to endoscope 42. However, care is taken not to draw the distal end of tubular member 22 and particularly capture web 26 with polyp P back into biopsy channel 40 of the endoscope. Polyp P remains in web or capture pocket 26 outside of tubular member 22 and endoscope 42 during the withrdawal of endoscope 42 from the patient.

Every polyp severed by a snare cauterization instrument as described and illustrated herein is captured immediately. Thus, the time for the capture and retrieval of severed polyps is reduced to a minimum. Trauma to patient is likewise reduced, as are hospitalization expenses.

Figure 3:
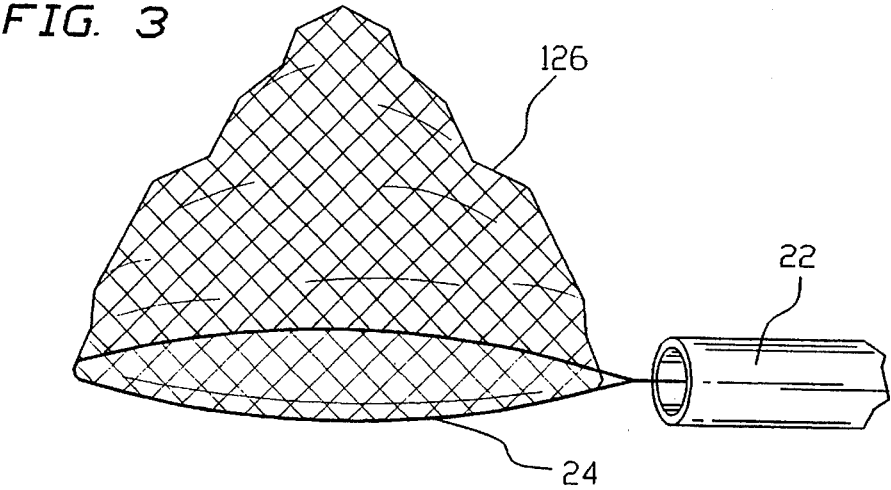
FIGS. 3–6 are schematic partial side perspective views, showing different specific embodiments of a snare cauterization instrument assembly.
Figure 4:
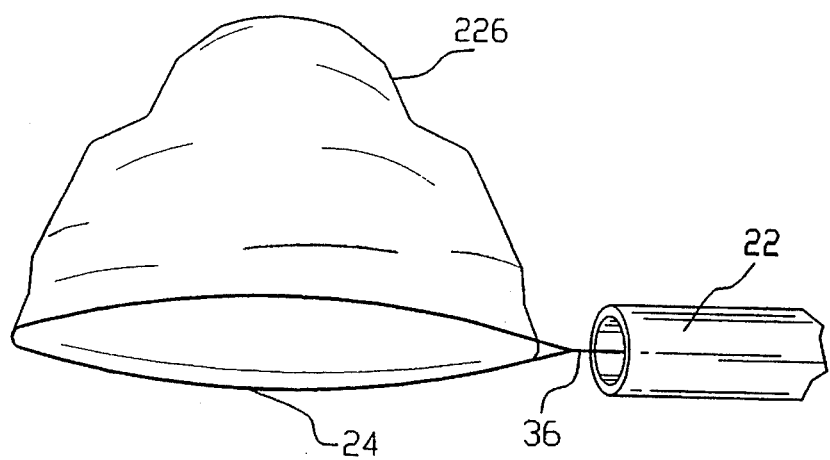
Figure 5:
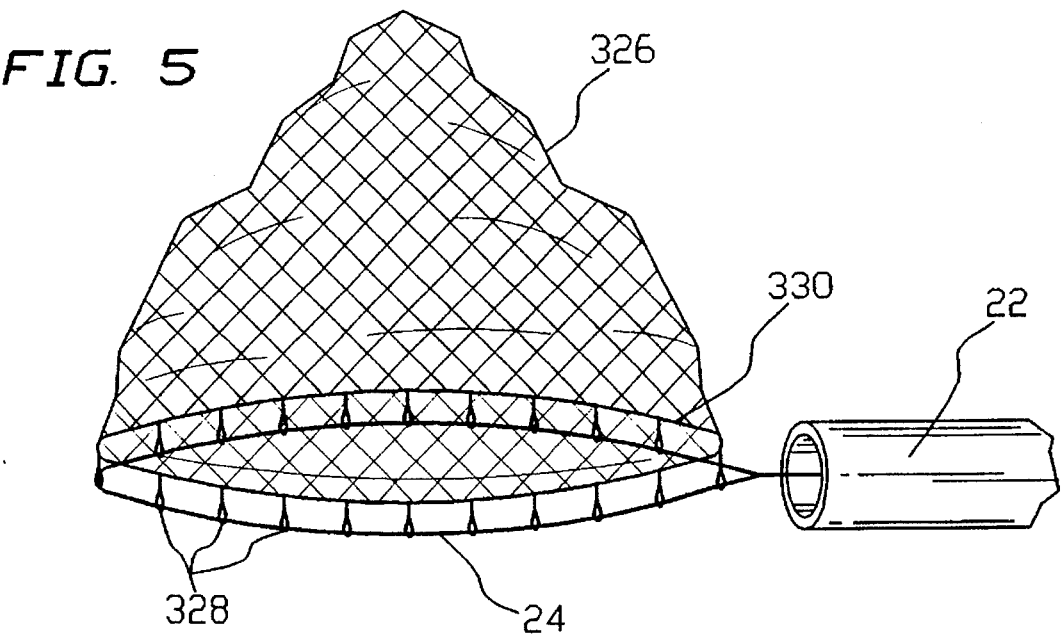
Figure 6:
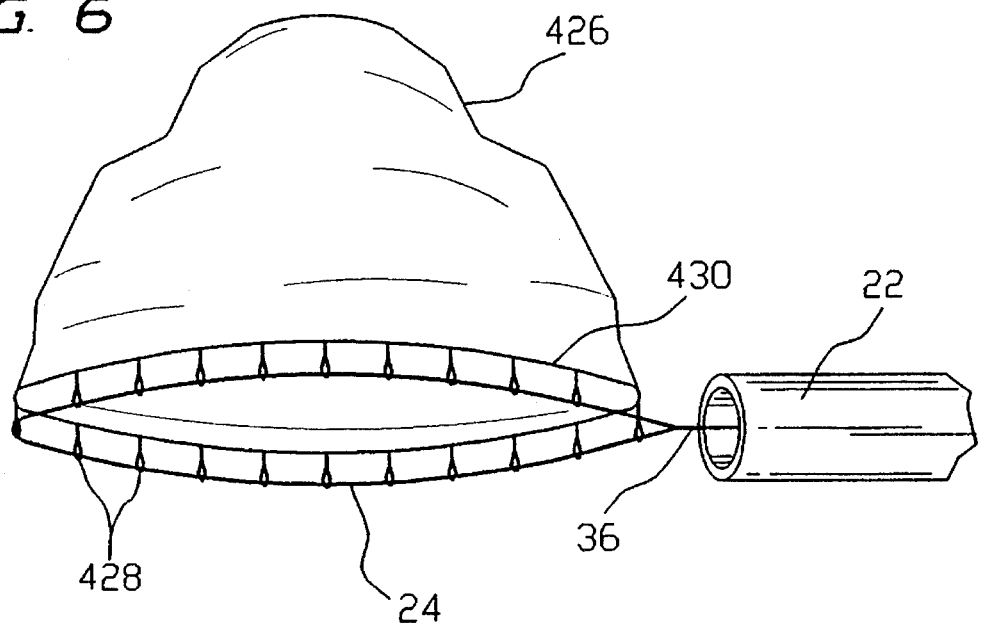

In FIGS. 3–6, like structural components bear the same reference designations. FIG. 3 shows a capture web 126 in the form of a net fastened directly to loop 24, while FIG. 4 shows a capture web 226 in the form of a continuous or solid transparent film fastened directly to loop 24. FIG. 5 illustrates a capture web 326 in the form of a net attached to loop 24 via a multiplicity of spaced ringlets 328. Loop 24 passes through ringlets 328, which are connected to a ring-shaped rim element 330 of web 326. Ringlets 328 are preferably made of a metallic material to facilitate the transmission of electrical current from cauterization loop 24 to the tie, sues of a polyp. FIG. 6 shows a capture web 426 in the form of a continuous or solid film of transparent polymeric material attached to loop 24 via a multiplicity of spaced ringlets 428. Loop 24 passes through ringlets 428, which are connected to a ring-shaped rim element 430 of web 326.

Figure 7:
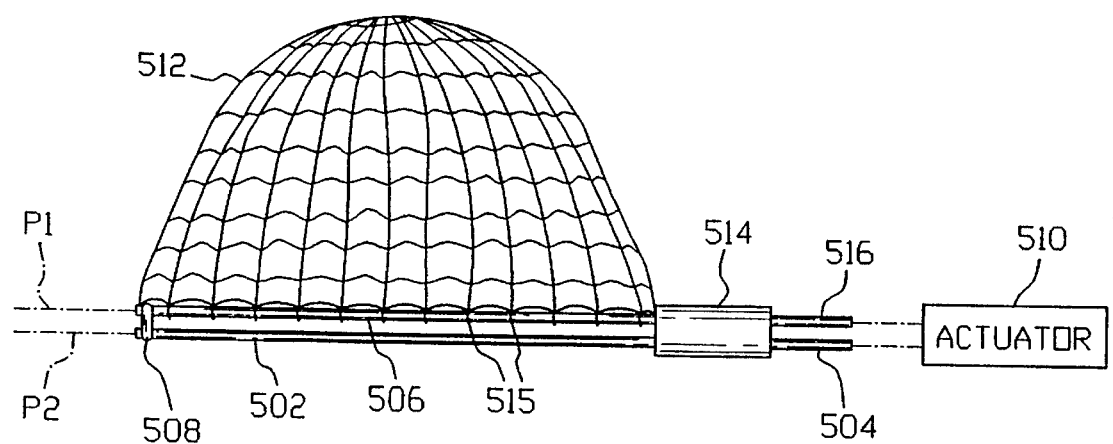
FIG. 7 is a schematic side elevational view, on an enlarged scale, of another embodiment of a snare cauterization instrument assembly, showing a pocket-defining web member on an auxiliary loop.

As illustrated in FIG. 7, a snare cauterization instrument assembly comprises a flexible cauterization loop 502, an electrical conductor 504 operatively connected to the cauterization loop for feeding an electrical current thereto, and a flexible auxiliary loop 506 connected via a fastening element 508 to the cauterization loop only at a distal end thereof. An actuator 510 is operatively connected to cauterization loop 502 and auxiliary loop 506 for alternately expanding and contracting the two loops in tandem with one another. A flexible web member 512 in the form of a net (or a continuous transparent membrane) is connected to auxiliary Loop 506 essentially around the circumference thereof to form a capture pocket, auxiliary loop 506 defining a mouth opening of the pocket. Preferably, net 512 is fixed to auxiliary loop 506 only at a distal end and a proximal end (inside a tubular sheath member 514) thereof, the remaining connections 515 being slidable.

Actuator 510 is connected to cauterization loop 502 via conductor 504, which functions in response to manipulations of actuator 510 to eject cauterization loop 502 from a collapsed storage position inside the distal end of tubular sheath member 514 and subsequently to pull cauterization loop back into the sheath member. Actuator 510 is coupled to auxiliary loop 506 via a flexible wire or rod member 516 which like conductor 504 extends longitudinally through sheath member 514.

Figure 8:
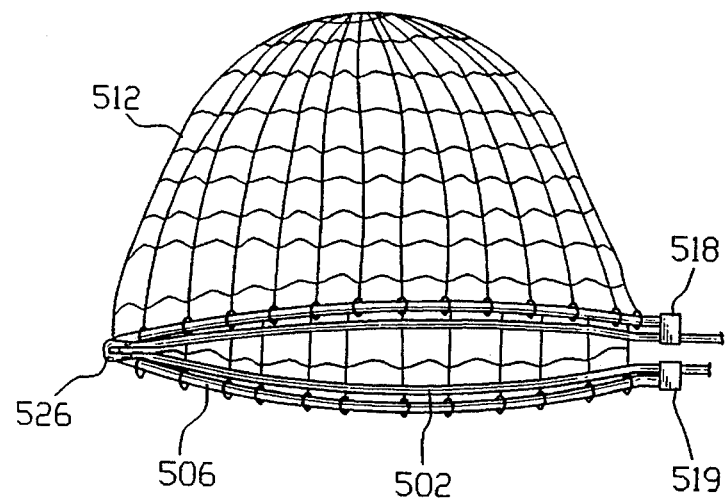
FIG. 8 is a schematic perspective view, also on an enlarged scale, of a modified snare cauterization instrument assembly, showing an auxiliary loop attached at three points to a cauterization loop.

Cauterization loop 502 and auxiliary loop 506 are disposed in parallel planes P1 and P2, respectively. As depicted in FIG. 8, auxiliary loop 506 may be connected at a proximal end to cauterization loop 502 at two points 518 and 519, as well as to the distal end of the cauterization loop. In that event, wire or rod member 516 may be omitted. As further shown in FIG. 8, auxiliary loop 506 is slightly larger than cauterization loop 502. The loops 502 and 506 are close, almost touching one another. As described above with reference to FIG. 7, web member 512 is fixedly connected to auxiliary loop 506 at a distal end and a proximal end thereof and slidably connected to the auxiliary loop between those ends.

FIG. 9 shows a cauterization loop 520 and an auxiliary loop 522 connected to one another at a distal end via a fastener 524. Cauterization loop 520 and auxiliary loop 522 are essentially coplanar in the expanded configuration illustrated in FIG. 9. During an ejection stroke and a subsequent retraction stroke of cauterization loop 520 and auxiliary loop 522 in response to the manipulations of an actuator (not shown) at a proximal end (not shown) of the instrument assembly, cauterization loop 520 and auxiliary loop 522 expand and contract in unison in essentially a common plane.

The embodiments of a cauterization snare instrument assembly illustrated in FIGS. 7–9 are less expensive to manufacture than the ringlet embodiments of FIG. 5 and 6 and enable use of a wider range of materials for the pocket or web member (512 in FIG. 7) than the embodiments of FIGS. 3 and 4. In addition, a primary advantage of the particular dual loop embodiments of FIGS. 7–9 is that auxiliary loops 506 and 522 are not connected to the cauterization loops 502 and 520 along operative portions thereof, thereby eliminating any possible interference that the auxiliary loops or capture nets 512 and 523 (FIG. 9) might otherwise exhibit with respect to the cutting and cauterization operations.

As illustrated in FIGS. 8 and 9, this elimination of possible interference in the cutting and cauterization operations is furthered by forming cauterization loops 502 and 520 at their distal ends with respective tongue-like extensions 526 and 528 to which auxiliary loops 506 and 522 are connected. Extensions 526 and 528 may be coated with an insulating material (not illustrated) and serve to separate fasteners 508 and 524 from the site of the cauterization procedure.

Auxiliary loops 506 and 522 are made of electrically nonconductive material preferably in the form of a synthetic resin or polymeric material such as polythylene or nylon.

In using the snare cauterization instrument assemblies of FIGS. 7–9, cauterization loop 502 or 520 and auxiliary loop 506 or 522 are expanded from a collapsed configuration inside the distal end of sheath member 514 to an expanded configuration. In the expanded configuration, auxiliary loop 506 or 522 is preferably larger than cauterization loop 502 or 520 and essentially parallel thereto. A special case of parallelism is found where the cauterization loop and the auxiliary loop are coplanar.

Pursuant to additional steps in the procedure, pocket or web member 512 is opened during the expansion of cauterization loop 502 or 520 and auxiliary loop 506 or 522 and the expanded loops are passed over a selected polyp or other internal tissue agglomeration to be removed, so that web member 512 substantially surrounds the polyp. Cauterization loop 502 or 520 is then closed by pulling it into the distal end of sheath member 514 or 528 (FIG. 9). The closure of cauterization loop 502 or 506 around a base region of the polyp while the cauterization loop is energized with electrical current serves to sever the polyp at its base. Maintaining web member 512 surrounding the polyp during the cauterization procedure serves to capture the severed polyp at the instant of its severance.

As illustrated in FIG. 10, a modified snare cauterization assembly includes a cauterization loop 530 surrounded along a substantial portion of its length by a tubular jacket or sleeve 532 to which a flexible pocket-defining web member 534 is connected. Jacket or sleeve 532 is made of a heat-conductive and electricity-conductive material enabling cauterization to proceed through the medium of the sleeve. In addition, sleeve 532 is provided with a coating or layer 535 of a biocompatible dye or ink material of a predetermined color. Color from coating 535 is transferred from the cauterization loop and particularly from sleeve 532 during the conduction of current through the loop. Coating 535 may be a liquifiable solid or a powder. Such a color-transferable coating or layer may be provided directly on any of the cauterization loops described herein. The deposition of a common color on a severed polyp and an unsevered neck or base area serves to facilitate a locating of the polyp's original situs upon a subsequent identification of the polyp as being malignant or a carcinoma. This is especially advantageous where several polyps are caught in the same procedure (see FIG. 15).

As illustrated in FIG. 11, another modified snare cauterization assembly comprises a cauterization loop 536 enclosed along essentially its entire length by a tubular jacket or sleeve 538 to which a flexible pocket-defining web member 540 is coupled. Sleeve 538 is provided along an inner side with a plurality of longitudinally extending windows 542 for facilitating or enabling the conduction of heat and/or electrical current from cauterization loop 536 to organic tissues of a polyp or other cell mass to be removed from a patient's body.

Figure 12:
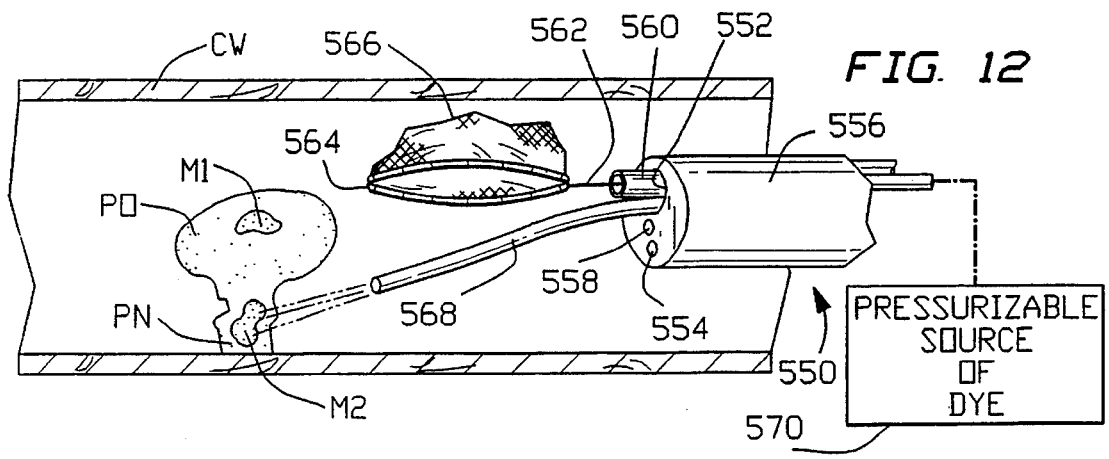
FIG. 12 is a schematic partial cross sectional view of a patient's colon with a polyp, showing a snare cauterization instrument assembly inserted through the biopsy channel of an endoscope which is itself inserted into the patient's colon, and further showing an instrument for depositing color markers on organic tissues.

As shown in FIG. 12, a surgical instrument assembly for use in a snare cauterization operations comprises an endoscope assembly 550 including a biopsy channel 552 and a light outlet 554 at a distal end of an endoscope insertion member 556 for delivering light to a surgical site inside a patient. The distal end of the endoscope insertion member 556 is further provided with a light inlet 558 for receiving light reflected from a surgical site. Light outlet 554 and light inlet 558 are located at the distal ends of a fiber optic illumination guide (not shown) and a fiber optic image guide (not shown), respectively, which extend longitudinally through endoscope insertion member 556.

As further illustrated in FIG. 12, a tubular sheath member 560 is inserted through biopsy channel 552, while a metal wire 562 passes longitudinally through the sheath 560 and is operatively connected at a distal end to an alternately expandable and collapsible metallic cauterization loop 564. An electrical supply (not shown in FIG. 12) is operatively connected to wire 562 for feeding an electrical current to loop 564 via the wire. A manually actuatable shifter (not illustrated in FIG. 12) is operatively connected to wire 562 at a proximal end thereof for longitudinally sliding the wire along sheath 560 in alternately opposite directions. A flexible web member 566 is connected to loop 564 to form a capture pocket, the loop defining a mouth opening of the pocket. Web member 566 is attached to loop 564 in a manner so as to expose the loop to enable effective cauterization of organic tissues by the loop.

Also extending through biopsy channel 552 is a tubular member 568 connected at a proximal end to a pressurizable dye or color source 570 such as a hypodermic syringe filled with a biocompatible liquid of a predetermined hue. A distal end portion of tubular member 568 is ejected from biopsy channel 552 upon arrival of the distal end of endoscope assembly 550 at an internal surgical site where a polyp PO is detected via light outlet 554 and light inlet 558 of endoscope assembly 550. Colored fluid is squirted from tubular member 568 to place recognizable markers M1 and M2 on polyp PO and a lower portion of a polyp neck PN by which polyp PO is connected to a colon wall CW of a patient. Markers M1 aand M2 enable subsequent identification of the original location of polyp PO upon a medical analysis of the polyp after it has been severed and removed from the patient in accordance with procedures described herein and other steps known to those skilled in the art.

Upon an insertion of endoscope insertion member 556 into a patient's colon, endoscope assembly 550 is used to visually monitor internal body tissues of the patient, including the internal surface of colon wall CW. Upon detecting selected internal body tissues (e.g., polyp PO) to be removed from the patient, loop 564 and web member 566 are ejected from a distal end of biopsy channel 552. Loop 564 and web member 566 are at least partially expanded from a collapsed configuration upon their ejection from biopsy channel 552. Loop 564 is manipulated from outside of the patient, e.g., via endoscope assembly 550 and more particularly via wire 562 or sheath 560, to pass the expanded loop over the polyp PO so that web member 566 substantially surrounds the polyp. Subsequently, loop 564 is closed to engage the polyp PO around a base region thereof. Closure is effectuated by sliding sheath 560 in a distal direction so that a proximal part of loop 564 is retracted into the sheath. An electrical current is conducted through the closed or partially closed loop 564 to burn through the base region of polyp PO, thereby severing the polyp PO at the base region. Loop 564 is closed further upon a completed burning of the loop through the base of the polyp PO, thereby capturing the severed polyp in web member or pocket 566.

Polyp PO and neck PN may be marked with a biocompatible dye or ink by tubular member 568 prior to the cauterization procedure. Alternatively, at least the neck portion PN may be marked after polyp PO has been severed by loop 564 and captured in web member 566. Tubular member 568 operates to spray a dterminable quantity of liquid dye or ink onto the surfaces of polyp PO and neck or base PN.

Figure 13:
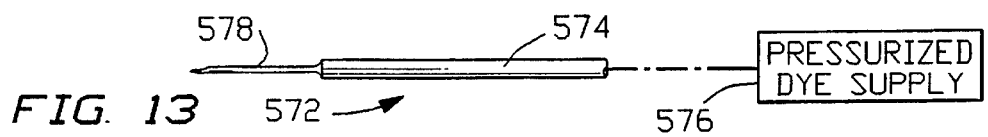
FIG. 13 is partially a schematic partial side elevational view and partially a block diagram of another color deposition instrument alternatively utilizable with the endoscopic snare cauterization instrument assembly of FIG. 12.

As illustrated in FIG. 13, another instrument 572 utilizable with endoscope assembly 550 to mark organic tissues inside a patient comprises a tubular member 574 operatively connected at a proximal end to a pressurized or pressurizable supply 576 of a biocompatible fluidic dye material. At a distal end, tubular member 574 is provided with a needle 578 for use in injecting the dye material below the surface of polyp PO and neck PN.

Figure 14:
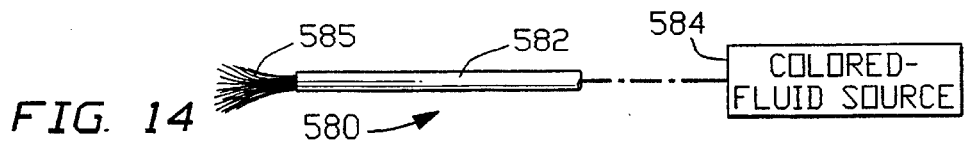
FIG. 14 is partially a schematic partial side elevational view and partially a block diagram of yet another color deposition instrument alternatively utilizable with the endoscopic snare cauterization instrument assembly of FIG. 12.

As shown in FIG. 14, another instrument 580 utilizable with endoscope assembly 550 to mark organic tissues inside a patient comprises a tubular member 582 operatively connected at a proximal end to a pressurized or pressurizable supply 584 of a biocompatible fluidic dye material. At a distal end, tubular member 582 is provided with a brush 585 for use in applying or painting the dye material on the surface of polyp PO and neck PN.

Figure 15:
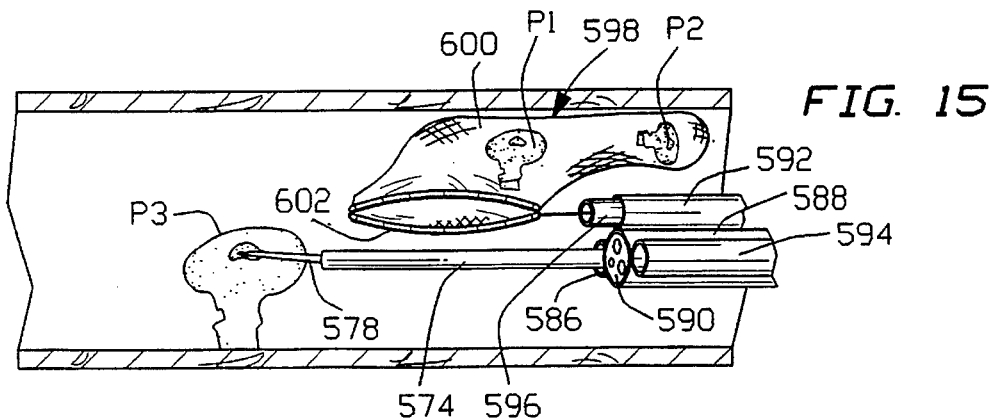
FIG. 15 is a schematic partial cross sectional view of a patient's colon with a polyp, showing a snare cauterization instrument assembly inserted through an alternately collapsible and expandable biopsy channel of an endoscope assembly which is itself inserted into the patient's colon, and further showing an instrument for depositing color markers on organic tissues.

Instrument 572 of FIG. 13 or instrument 580 of FIG. 14 may be inserted through biopsy channel 552 of endoscope assembly 550. Alternatively, tubular member 568 or marking instrument 572 or 580 may be inserted through an alternately expandable and collapsible biopsy channel 586 provided on a sheath 588 surrounding an endoscope insertion member 590, as illustrated in FIG. 15. Such an endoscope sheath 588 may take the form described and illustrated in U.S. Pat. Nos. 4,646,722 and 5,025,778, the disclosures of which are hereby incorporated by reference.

Sheath 588 is provided with other alternately expandable and collapsible biopsy channels 592 and 594, one of which receives a sheath 596 of a cauterization instrument assembly 598. As depicted in FIG. 15, an expanded web member 600 at a distal end of instrument assembly 598 carries a pair of polyps P1 and P2 which have already been marked with respective colors and severed. FIG. 15 shows a third polyp P3 being marked by instrument 572 (FIG. 13) prior to cauterization and severing by a loop 602 to which web member 600 is attached in a manner to enable cauterization by the loop.

Figure 16:
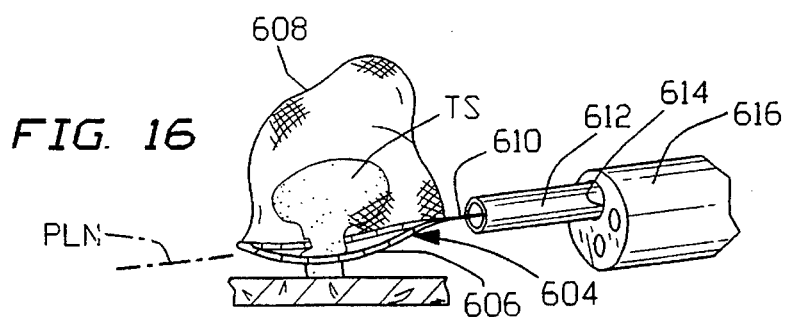
FIG. 16 is a schematic perspective view of a distal end portion of an endoscopic cauterization instrument assembly, showing a cauterization loop of the assembly in use to cauterize and sever a polyp in a patient's colon.

As shown in FIG. 16, another assembly for use in severing and removing an organic tissue sample TS from inside a patient comprises a cauterization loop 604 which in an expanded configuration has a bent configuration which arcs at 606 laterally from a plane PLN in which the loop opens and closes. Arc or curvature 606, inherent in the prestressed or spring-biased construction of loop 604, facilitates the capture of polyps by facilitating the encirclement thereof, as indicated in FIG. 16. The curved design of FIG. 16 may be used in any of the snare embodiments described herein, as well as in prior art cauterization loops without an attached capture pocket or web. Loop 604 is provided with a capture pocket 608 and is operatively connected to an eletrical energy source (not shown) via an elongate wire 610 extending longitudinally through a sheath 612 in turn extending through a biopsy channel 614 of an endoscope isnertion member 616.

It is to be noted that colored staples may be used to mark a polyp and/or its base, the staples being applied via an endoscopic stapling instrument as disclosed in U.S. Pat. Nos. 5,015,249 and 5,049,153 and 5,156,609, the disclosures of which are hereby incorporated by reference. The staples may be applied to the base or neck of a severed polyp either before or after a cauterization procedure.

As illustrated in FIGS. 17 and 18, an endoscopic cauterization snare surgical instrument 700 comprises a tubular sheath member 702, an alternately expandable and contractible cauterization loop 704, and an electrically conductive wire 706 operatively connected to loop 704. Wire 706 is slidable longitudinally through sheath member 702. A flexible web member 708 in the form of a net or film is connected to loop 704 essentially around a circumference thereof to form a capture pocket. Loop 704 defines a mouth opening of the pocket which is attached to loop 704 in a manner so as to expose the loop to enable effective cauterization of organic tissues by the loop. Web member 708 is removably attached to loop 704 to enable a separation of web member 708 from loop 704 upon a proximally directed stroke of wire 706 at the termination of a cauterization operation.

A purse string 710 is attached to web member 708 along a ring shaped locus proximately to the mouth opening of the capture pocket, i.e., proximately to loop 704. A proximal end strand or strands 712 of purse string 710 are attached at 714 to wire 706, proximately to the distal end thereof. Alternatively, purse string end strands 712 may extend in a proximal direction entirely through sheath member 702 to the proximal end thereof.

Web member 708 is attached by adhesive 716 (FIG. 18) to loop 704, either at a plurality of discrete points 718 (FIG. 17) or along a continuous length of loop 704. It is contemplated that web member 708 is removably attached to loop 704 along a radially outwardly facing surface area 720 of loop 704 (FIG. 18).

As discussed above, web member 708 may be the form of a net, or alternatively in the form of a continuous film of polymeric material.

In using the cauterization snare assembly 700 of FIGS. 17 and 18, loop 704 is ejected from a distal end of sheath member 702 which in turn is elected from a biopsy channel 724 of a flexible endoscope 726. Upon ejection of loop 704, loop 704 and web member 708 are expanded from a collapsed configuration to an at least partially opened configuration, as shown in FIG. 19A. As further shown in that drawing figure, expanded loop 704 is passed over the selected internal body tissues ST to be removed, so that web member 708 substantially surrounds the selected internal body tissues ST. Subsequently, as illustrated in FIG. 19B, loop 704 is drawn back into the distal end of sheath member 702, thereby closing loop 704 around a base region BR of the selected internal body tissues, while web member 708 is maintained surrounding the selected internal body tissues ST (e.g., polyp). During the drawing of loop 704 back into sheath member 702, an electrical current is conducted through loop 704 to sever the selected internal body tissues at base region BR. In addition, web member 708 is detached from loop 704 during the drawing of loop 704 back into sheath member 702 so that web member 708 remains outside sheath member 702, as depicted in FIG. 19C. The mouth opening of web member 708 is closed during the severing operation to thereby capture the severed internal body tissues ST in web member 708.

Web member 708 is detached by being peeled away from loop 704 at a distal edge 728 of sheath member 702. The drawing of loop 704 back into the distal end of sheath member 702 draws the capture pocket into contact with distal edge 728. That contact forces the capture pocket or web member 708 from loop 704.

Loop 704 is pulled completely into sheath member 702 (FIG. 19C) upon the termination of a cauterization operation. Web member 708 and the captured internal body tissues remain outside of sheath member 702.

Figure 20A:
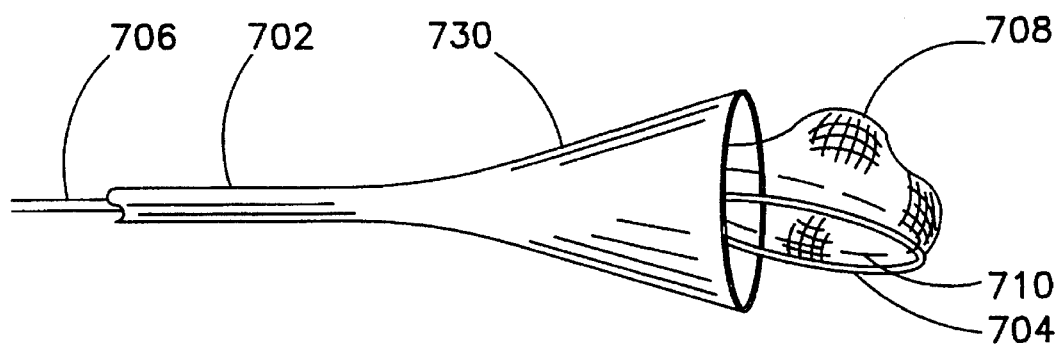
FIGS. 20A and 20B are schematic side elevational views of a snare assembly, showing successive steps in a manufacturing process in accordance with the present invention.
Figure 20B:
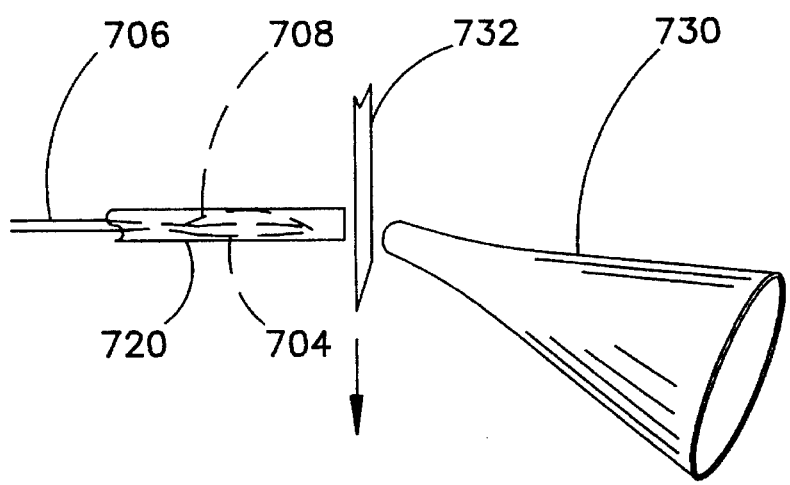

As illustrated in FIG. 20A, cauterization loop 704 with its attached web member or capture pocket 708 is inserted into the distal end of sheath member 702 by initially providing the sheath member with a flared distal end portion 730. Upon a pulling of wire 706 in a proximal direction through sheath member 702, capture pocket or web member 708 is gradually compressed into a collapsed configuration. When the loop 704 and web member 708 have reached the narrowed end of sheath member 702, as shown in FIG. 20B, flared end portion 730 is severed by a blade 732 and discarded.

The material of a capture pocket as described herein must be biocompatible and should be heat resistant as well. In addition, it is contemplated that the material of the capture pocket has a memory as well, so that when the cauterization loop and the capture pocket are ejected from the distal end of a sheath, the capture pocket springs open, ready for use.

Figure 21A:
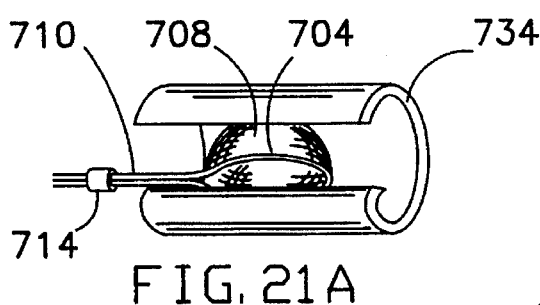
FIGS. 21A and 21B are schematic perspective views of a snare assembly, showing successive steps in another manufacturing process in accordance with the present invention.
Figure 21B:
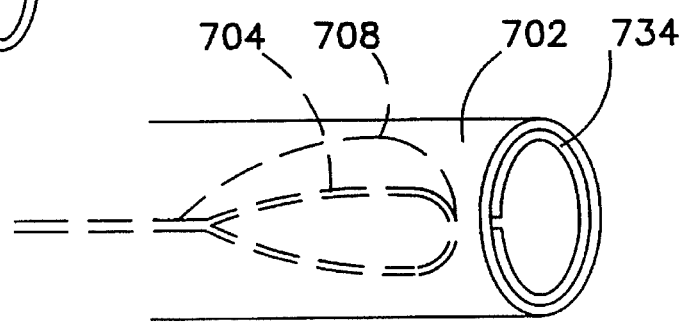

FIGS. 21A and 21B depict another method for disposing cauterization loop 704 with its attached web member or capture pocket 708 in the distal end of sheath member 702. Loop 704 and web member or capture pocket 708 are wrapped in a thin film 734, as shown in FIG. 21A. The entire assembly, including loop 704, pocket 708 and film 734 is then slid into the distal end of sheath member 702, as shown in FIG. 21B. Film 734 may be bonded to the inner surface of sheath 702, for example, by heat, adhesive, or ultrasonic welding.

Figure 22:
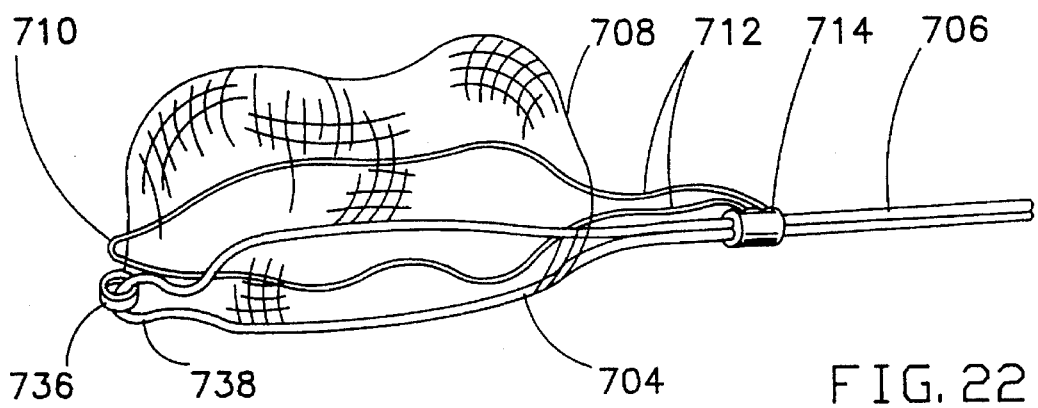
FIG. 22 is a schematic side elevational view, similar to FIG. 17, showing a modification of the snare assembly of that drawing Figure.
Figure 23:
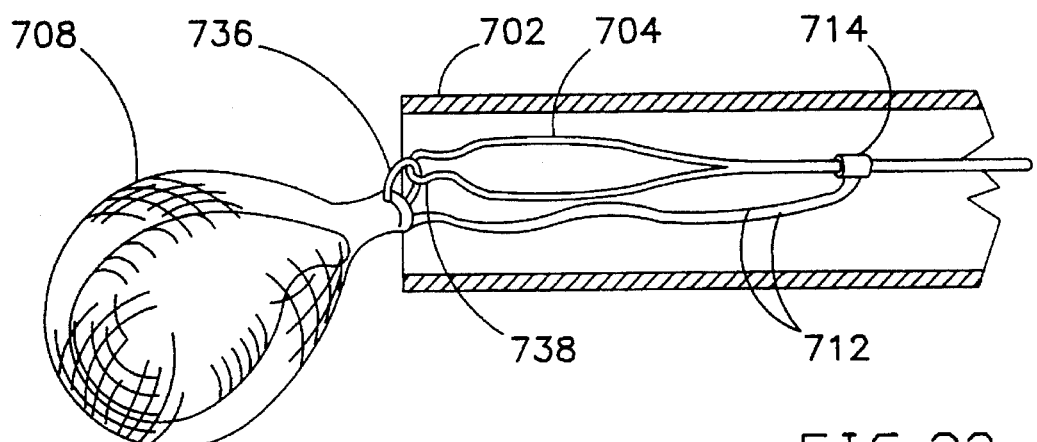
FIG. 23 is partially a cross-sectional view of a sheath and partially a side elevational view of the modified snare assembly of FIG. 22, at the termination of a polypectomy procedure in accordance with the present invention.

As illustrated in FIGS. 22 and 23, web member or capture pocket 708 may be additionally provided, at a distal end only, with a permanent attachment 736 to cauterization loop 704, particularly at a distal finger-like extension 738 thereof. This permanent attachment may be in the form of a ringlet, a series of wound threads, a spot of adhesive, etc. Attachment 736 serves to facilitate insertion of loop 704 with pocket 708 into sheath 702 from the proximal end thereof. Attachment 736 prevents separation of capture pocket 708 from loop 704 during the insertion procedure and additional provided extra assurance that the capture pocket will not become detached from loop 704 while inside the patient.

FIG. 23 shows a step at the termination of a polypectomy procedure, where capture pocket 708 is substantially separated from loop 704 but is retained thereon by virtue of attachment 736.

Figure 24:
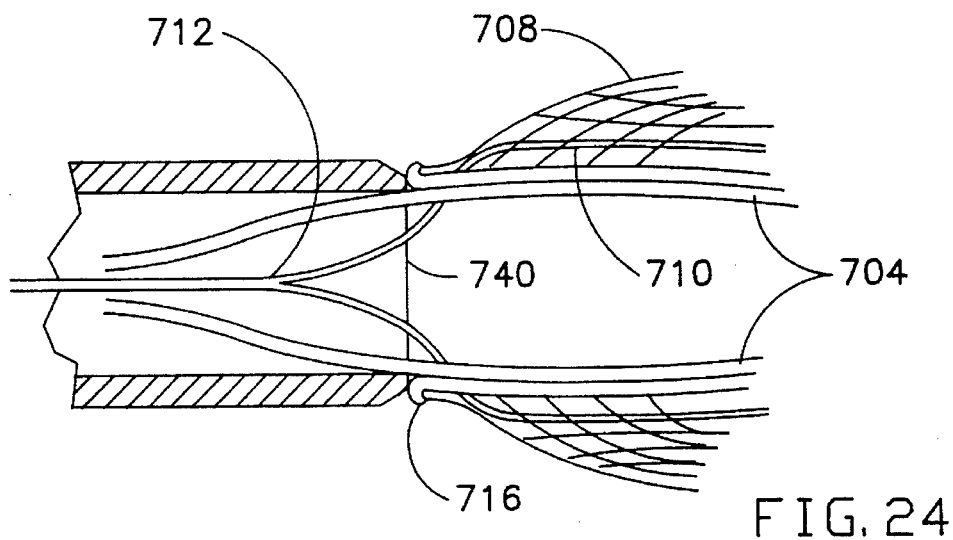
FIG. 24 is partially a cross-sectional view of a modified sheath and partially a side elevational view of the snare assembly of FIGS. 17, 18, and 19A–19C, showing an early stage in a retraction of loop 704 and pocket 708 into the sheath.

As depicted in FIG. 24, sheath 702 may be provided at a distal end with a sharp edge 740, formed by beveling the sheath. Edge 740 serves to facilitate separation of capture pocket 708 from loop 704 by cutting into adhesive 716 along radially outwardly facing surface area 720 of loop 704 (see FIG. 18).

Figure 25A:
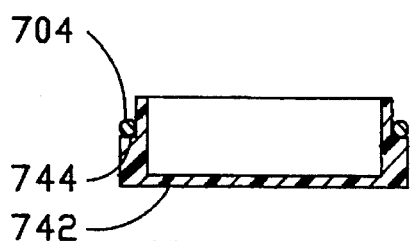
FIGS. 25A–25C are schematic cross-sectional views of a cauterization loop holder, showing successive steps in a manufacturing process.
Figure 25B:
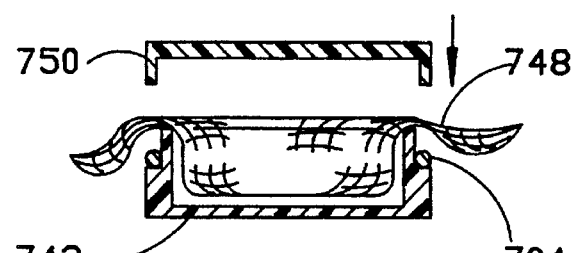
Figure 25C:
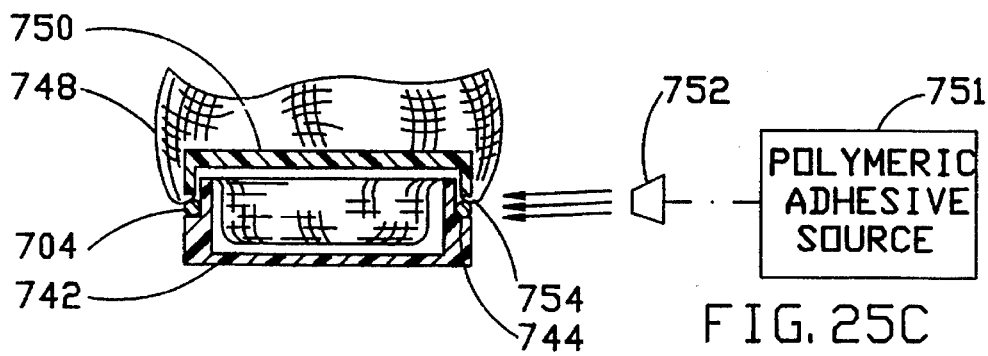

In manufacturing a cauterization snare in accordance with the present invention, loop 704 is placed around a cylindrical container or holder 742 so that a radially inward facing surface portion of the loop is in contact with the holder, as shown in FIG. 25A. Holder 742 has a circular shoulder 744 along a cylindrical outer surface. Shoulder 744 serves to support 704 loop in a predetermined position. A knitted net or web 748 is then pushed into holder 742, as shown in FIG. 25B, to provide extra material to form a pocket. A cap 750 is placed over the container, as indicated in FIGS. 25B and 25C. Net 748 is folded back from the edge of cap 750 (FIG. 25C), thereby positioning the net material a predetermined distance from shoulder 744, and accordingly from loop 704. An adhesive or polymeric material such as PARYLENE from a reservoir or source 751 is applied, e.g., sprayed, via a nozzle 752 or other applicator into a gap 754 between loop 704 and the folded back flap of net material 748. The adhesive or polymeric material such as PARYLENE sticks to the loop 704 and the net material, but not to the container or holder. After application of the adhesive or polymeric material, excess net material is cut off along a circular arc and the loop with the attached pocket is removed from the container or holder.

Figure 26:
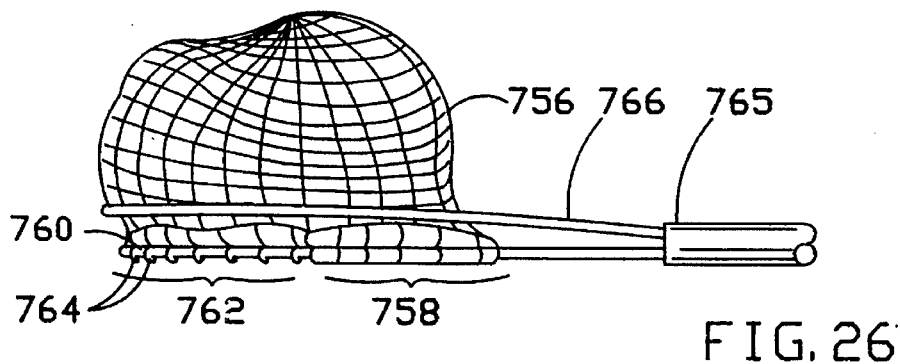
FIG. 26 is a schematic side elevational view of a modified cauterization snare with capture pocket, in accordance with the present invention, showing a cauterization loop and a pocket completely extended from a tubular sheath.
Figure 27:
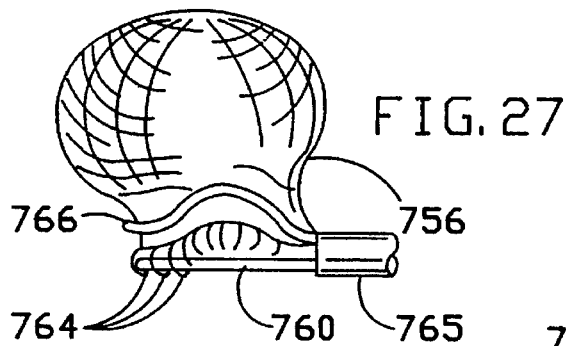
FIG. 27 is a schematic side elevation view of the modified cauterization snare and capture pocket of FIG. 26, showing partial retraction of the loop into the sheath and a concomitant dissociation of the capture pocket from the loop.

As depicted in FIG. 26, a capture pocket 756 is connected along a proximal side 758 of a cauterization loop 760 via a polymeric adhesive such as PARYLENE (not designated). Capture pocket 756 is connected along a distal side 762 of loop 760 via a plurality of filaments 764. During a polyp cauterization procedure as described hereinabove, pocket 756 is separated from the proximal side 758 of loop 760 owing to a peeling away of the polymeric adhesive layer during a retraction of loop 760 into the distal end of a sheath 765. This peeling away of the adhesive layer, and the concomitant partial dissociation of pocket 756 from loop 760, occurs generally before the conduction of current through loop 760 and the consequent severing of a polyp. During a later stage of the polyp severing and retrieval procedure, filaments 764 are burned off of cauterization loop 760, as shown in FIG. 27. Pocket 756 accordingly separates from loop 760 during the cauterization procedure. Pocket 756 is maintained in a closed state, holding a captured polyp (not shown), by virtue of a purse string 766, which functions as described hereinabove with reference to FIGS. 17 through 19C.

In an alternate configuration, pocket 756 may be connected to loop 760 solely by filaments 764 which are burned off or otherwise severed during a cauterization operation, thereby freeing the capture pocket from loop 760.

Figure 28:
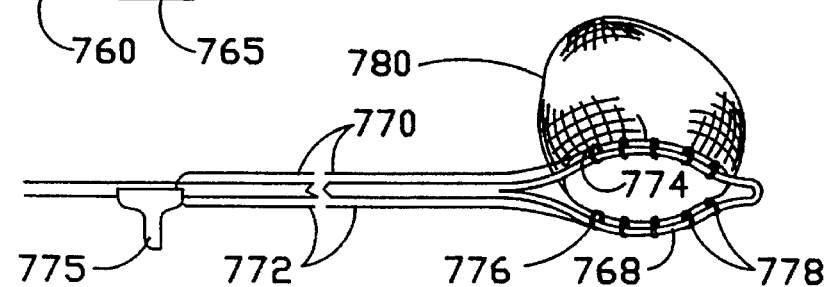
FIG. 28 is a schematic perspective view of another cauterization loop with a capture pocket, in accordance with the present invention.

FIG. 28 illustrates an embodiment of the invention which provides the possibility of repeated ejections and retractions of a cauterization loop 768 relative to a sheath (not illustrated) prior to a cauterization and severing of a polyp. This provides the practitioner with the capability of adjusting the location of the snare on a target polyp prior to completing the surgical severing operation. As illustrated in FIG. 28, two threads 770 and 772 are connected at their respective proximal ends to a slider member 775 which is disposed on a handle (not illustrated) of the snare. At their distal ends, threads 770 and 772 are connected to respective ringlets 774 and 776 which are slidably coupled to loop 768 proximally of other ringlets 778.

Upon a retraction of loop 768 and a consequent sliding of ringlets 774, 776, 778 along the loop to a distal side thereof after a surrounding of a polyp (not shown) with a capture pocket 780 on loop 768, the practitioner may decide that loop 768 is not optimally positioned on the neck of the polyp. Loop 768 is then ejected again from its sheath. In order to open pocket 780 and properly position the pocket along loop 768, the practitioner shifts slider member 775 in the proximal direction and thereby pulls ringlets 774 and 776 back towards the proximal end of loop 768.

Figure 29A:
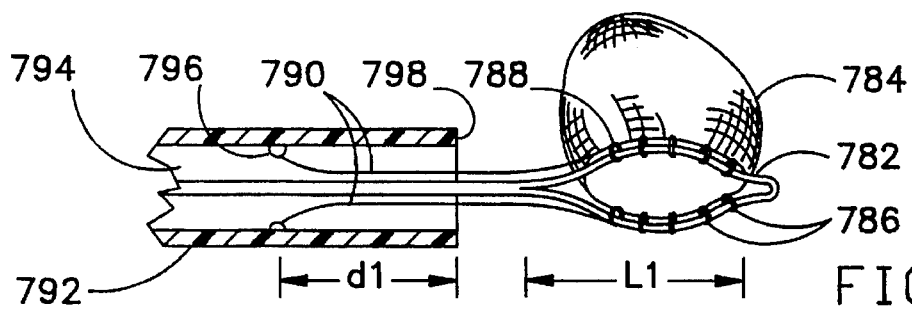
FIGS. 29A–29C are schematic side perspective views, partially in cross-section, of another modified cauterization snare and capture pocket in accordance with the present invention, showing three steps in the use of the device.
Figure 29B:
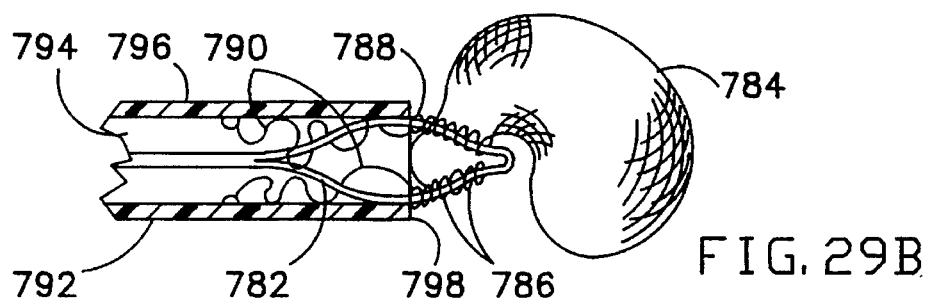
Figure 29C:
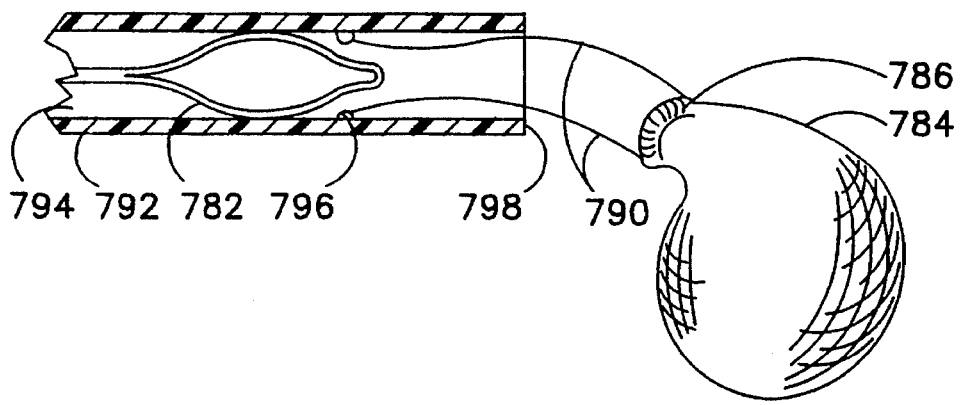

FIGS. 29A–29C illustrate steps in using a modified snare including a cauterization loop 782 with a capture pocket 784 attached by burnable ringlets 786 to the loop. Two most proximal ringlets 788 are connected via respective threads 790 to an inner surface or side 794 of a deployment sheath 792. Points of connection 796 of threads 790 to sheath surface 794 are located at a distance d1 from the distal tip 798 of sheath 792 approximately equal to half of the length L1 of loop 782.

Upon an extension of loop 782 from sheath 792, as illustrated in FIG. 29A, threads 790 pull ringlets 788 in a proximal direction to the proximal side of loop 782, thereby stretching capture pocket 784 out to an optimally opened configuration. Of course, threads 790 also limit the extent to which loop 782 may be distanced from the distal end of sheath 792.

FIG. 29B shows the sliding of ringlets 786 and 788 in a distal direction relative to loop 782 upon a retraction of the loop into sheath 792, after loop 782 and pocket 784 have been placed about a polyp (not shown). In the event that the user endoscopist decides that an adjustment of the snare relative to the polyp is desired, loop 782 is pushed in a distal direction relative to sheath 792. This movement may be accomplished, of course, by pulling sheath 792 in a proximal direction relative to loop 782. Upon a sufficient ejection of loop 782 from sheath 792, threads 790 again pull ringlets 788 in a proximal direction to the proximal side of loop 782 to thereby open capture pocket 784.

If the user endoscopist decides that loop 782 is propitiously positioned relative to the subject polyp, loop 782 is pulled further into sheath 792, as illustrated in FIG. 29C. Ringlets 786 and 788 are severed from loop 782 via a burning process, thereby freeing capture pocket 784 from loop 782. The polyp cauterization assembly of FIGS. 29A–29C may be provided with a purse string (net illustrated) as described above with reference to FIGS. 17–19C, for ensuring closure of capture pocket 784 upon completion of a polyp severing operation.

Figure 30:
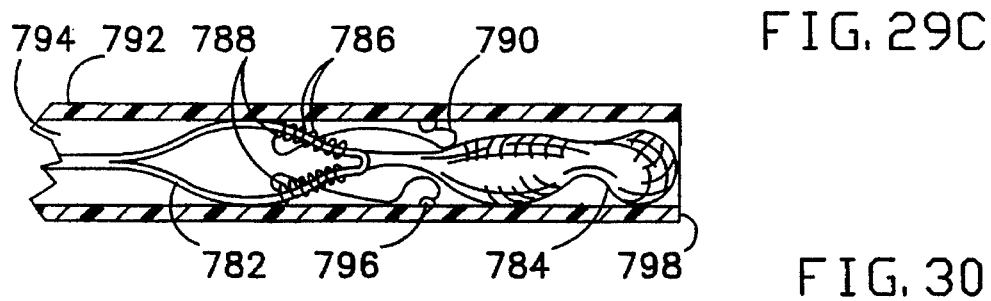
FIG. 30 is a schematic side elevational view, partially in cross-section, showing the cauterization snare and capture pocket of FIGS. 29A–29C in a retracted pre-firing insertion configuration.

As shown in FIG. 30, in packing loop 782 and pocket 784 inside sheath 792, pocket 784 may be disposed distally of loop 782, thereby facilitating the packaging process.

Figure 31:
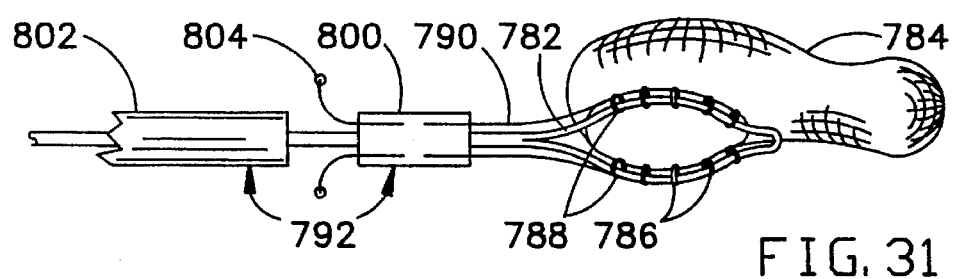
FIG. 31 is a schematic side elevation view showing a stage in the assembly of the cauterization snare and capture pocket of FIGS. 29A–29C and 30.

FIG. 31 illustrates a step in a manufacturing operation. Sheath 792 includes a distal segment 800 which is attached to a body portion 802 of the sheath via ultrasonic welding, adhesive, heating, or other process. Threads 790 extend through segment 800 and are sandwiched between segment 800 and body portion 802 upon connection of those sheath elements to one another. Threads 790 may be provided additionally with knots 804 which are located outside of the sheath 792 upon completion of manufacturing. Knots 804 serve as anchors, preventing dislodgement of threads 790 during use of the cauterization snare assembly.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An endoscopic surgical instrument for use in snare cauterization operations, comprising:

a tubular sheath member;

loop means made at least in part of an electrically conductive material for forming an alternately expandable and contractible cauterization loop;

an electrically conductive wire operatively connected to said loop means and extending longitudinally through said sheath member, said wire being slidable longitudinally through said sheath;

electrical connector means at a proximal end of said wire for coupling said wire to a source of electrical energy;

a flexible web member connected to said loop means essentially around a circumference thereof to form a capture pocket, said loop means defining a mouth opening of said pocket, said web member being attached to said loop means in a manner so as to expose said loop means to enable effective cauterization of organic tissues by said loop means, said web member being removably attached to said loop means along a major portion thereof; and means on said sheath member at a distal end thereof for at least substantially separating said web member from said loop means upon a proximally directed stroke of said wire at the termination of a cauterization operation.

2. The instrument defined in claim 1, further comprising a purse string attached to said web member along a ring shaped locus proximately to said mouth opening.

3. The instrument defined in claim 2 wherein said purse string is attached at a proximal end to said wire.

4. The instrument defined in claim 1 wherein said web member is attached by adhesive to said loop means.

5. The instrument defined in claim 1 wherein said web member is attached at a plurality of discrete points to said loop means.

6. The instrument defined in claim 1 wherein said loop means has a radially outwardly facing surface area, said web member being removably attached to said loop means along said surface area.

7. The instrument defined in claim 1 wherein said web member is a net.

8. The instrument defined in claim 1 wherein said web member is a continuous film of polymeric material.

9. The instrument defined in claim 1, further comprising means for permanently connecting said web to said loop means only at a distal tip thereof.

10. A method for removing a selected portion of internal body tissues of a patient, comprising the steps of:

providing a conductive cauterization loop to which a flexible web member is removably connected to define an expandable pocket, said loop defining a mouth opening of said pocket, said web member being attached to said loop in a manner so as to expose said loop to enable effective cauterization of organic tissues by said loop;

ejecting said loop from a distal end of a tubular sheath member;

upon said step of ejecting, expanding said loop and said web member from a collapsed configuration to an at least partially opened configuration;

passing the expanded loop over the selected internal body tissues to be removed, so that said web member substantially surrounds said selected internal body tissues;

drawing said loop back into said distal end of said tubular sheath member, thereby closing said loop around a base region of said selected internal body tissues, while said web member is maintained surrounding said selected internal body tissues;

during said step of drawing, conducting an electrical current through said loop to sever said selected internal body tissues at said base region;

during said step of drawing, detaching said web member from said loop so that said web member remains outside said sheath member; and also during said step of drawing, closing said mouth opening of said web member to thereby capture the severed internal body tissues in said web member.

11. The method defined in claim 10 wherein said step of detaching includes the step of peeling said web member away from said loop at a distal edge of said sheath member.

12. The method defined in claim 10 wherein said step of expanding comprising the step of pushing said loop, together with said web member, from a distal end of said sheath member.

13. The instrument defined in claim 10 wherein said loop is pulled completely into said sheath member during said step of drawing, said web member and the captured internal body tissues remaining outside of said sheath member.

14. An endoscopic surgical instrument for use in snare cauterization operations, comprising:

a tubular sheath member;

loop means made at least in part of an electrically conductive material for forming an alternately expandable and contractible cauterization loop;

an electrically conductive wire operatively connected to said loop means and extending longitudinally through said sheath member, said wire being slidable longitudinally through said sheath;

a flexible well member connected to said loop means essentially around a circumference thereof to form a capture pocket, said web member being attached by adhesive to said loop means, said loop means defining a mouth opening of said pocket, said web member being attached to said loop means in a manner so as to expose said loop means to enable effective cauterization of organic tissues by said loop means, said web member being removably attached to said loop means along a major portion thereof; and means on said sheath member at a distal end thereof for at least substantially separating said web member from said loop means upon a proximally directed stroke of said wire at the termination of a cauterization operation.

15. An endoscopic surgical instrument for use in snare cauterization operations, comprising:

a tubular sheath member;

loop means made at least in part of an electrically conductive material for forming an alternately expandable and contractible cauterization loop;

an electrically conductive wire operatively connected to said loop means and extending longitudinally through said sheath member, said wire being slidable longitudinally through said sheath member;

a flexible wed member connected to said loop means essentially around a circumference thereof to form a capture pocket, said loop means defining a mouth opening of said pocket, said web member being attached to said loop means in a manner so as to expose said loop means to enable effective cauterization of organic tissues by said loop means, said web member being removably attached to said loop means along a major portion thereof;

means for permanently connecting said web to said loop means only at a distal tip thereof; and means on said sheath member at a distal end thereof for at least substantially separating said web member from said loop means upon a proximally directed stroke of said wire at the termination of a cauterization operation.

* * * * *